(12) United States Patent
Aden

(10) Patent No.: US 6,273,857 B1
(45) Date of Patent: Aug. 14, 2001

(54) METHOD AND SYSTEM FOR CORRELATING EXAM WORKSHEET VALUES TO SUPPORTING MEASUREMENTS

(75) Inventor: Michael Aden, Bellevue, WA (US)

(73) Assignee: Siemens Medical Systems, Inc, Iselin, NJ (US)

( * ) Notice: Subject to any disclaimer, the term of this patent is extended or adjusted under 35 U.S.C. 154(b) by 0 days.

(21) Appl. No.: 09/361,687

(22) Filed: Jul. 27, 1999

(51) Int. Cl.[7] ....................................... A61B 8/00

(52) U.S. Cl. ............................ 600/437; 600/449

(58) Field of Search ................... 600/437, 438, 600/443, 447, 448, 449, 444

(56) References Cited

U.S. PATENT DOCUMENTS

| 5,588,435 | 12/1996 | Weng et al. | 128/660.07 |
| 5,605,155 | * 2/1997 | Chalana et al. | 600/443 |
| 5,715,823 | * 2/1998 | Wood et al. | 600/437 |
| 5,795,297 | * 8/1998 | Diagle | 600/447 |
| 5,838,592 | 11/1998 | Spratt | 364/560 |
| 5,851,186 | 12/1998 | Wood et al. | 600/437 |
| 5,860,931 | 1/1999 | Chandler | 600/458 |

* cited by examiner

Primary Examiner—Marvin M. Lateef
Assistant Examiner—Maulin Patel

(57) ABSTRACT

A method and a system for storing and managing dimensional measurement values and the underlying ultrasound images utilize a report generator that operates to generate an examination report of an ultrasound examination having saved measurement values. The examination report allows for an expedient access to the corresponding ultrasound images that were used to derive the measurement values. In addition, the report generator operates to automatically save the ultrasound image when a measurement value that was computed from that ultrasound image is saved. This feature ensures that for each saved measurement value, the corresponding ultrasound image is also saved. The system utilizes ultrasound waves to image various anatomical features of a patient or a fetus. Examples of anatomical features that may be imaged by the system include the femur, the humerus and the head of a fetus. These ultrasound images are used to compute measurements of the anatomical features. In one embodiment, the examination report generated by the report generator and displayed on a display device of the system contains a number of virtual buttons that are associated with the saved measurement values. When a virtual button is activated, the corresponding ultrasound image of the measurement value that is associated with the activated virtual button is displayed on the display device. In another embodiment, the virtual buttons are replaced by hyperlinks. The virtual buttons or the hyperlinks facilitate expedient access to a particular ultrasound image that corresponds to a measurement value on the examination report that is of interest.

22 Claims, 6 Drawing Sheets

MEASUREMENT VALUES

| 7.0 cm<br>Femur Length 001 (✓) ~58 | 6.9 cm<br>Femur Length 002 ~58 | 6.7 cm<br>Femur Length 003 ~58 | 8.1 cm<br>Femur Length 004 ~58A |
|---|---|---|---|
| # cm<br>Head Circumference 001 ( ) ~60 | # cm<br>Head Circumference 002 (✓) ~60 | # cm<br>Head Circumference 003 (✓) ~60 | # cm<br>Head Circumference 004 ( ) ~60 |
| # cm<br>Humerus Length 001 ( ) ~62 | # cm<br>Humerus Length 002 (✓) ~62 | # cm<br>Humerus Length 003 ( ) ~62 | # cm<br>Humerus Length 004 ( ) ~62 |

FIG. 5

METHOD AND SYSTEM FOR CORRELATING EXAM WORKSHEET VALUES TO SUPPORTING MEASUREMENTS

TECHNICAL FIELD

The invention relates generally to ultrasound imaging and more particularly to a method and a system for measuring body structures using ultrasound imaging.

DESCRIPTION OF THE RELATED ART

Ultrasound imaging systems are commonly used to measure various anatomical features of a human fetus during fetal development. The measurements of the anatomical features may include the femur length, the humerus length, and the head circumference of the fetus. These measurements can be used to determine the gestational age of the fetus. The gestational age can then be used to assist in a diagnosis of the fetus with respect to abnormalities by comparing the different measurements with established values for that gestational age.

During an ultrasound examination using a conventional ultrasound imaging system, measurement values are computed by examining a "freeze frame" of a scanned ultrasound image displayed on a monitor of the system. The "freeze frame" includes the anatomical feature of the fetus that is to be measured. Typically, a line or an ellipse is drawn over the displayed anatomical feature to measure the length or the circumference of the anatomical feature. After the computation, the measurement value and the corresponding ultrasound image that was used to compute the measurement value can be independently stored in the system. Thus, storing both the measurement value and the corresponding ultrasound image requires two steps, one step to store the measurement value and another step to store the corresponding ultrasound image. If the ultrasound image is not stored at this time, that particular ultrasound image is generally discarded and cannot be stored at a later time. For a specific anatomical feature of a fetus, anywhere from three to six measurements are typically made.

Since the corresponding ultrasound image may not have been saved for each stored measurement value, it may not be possible to verify, at a later time, the measurement values that were selectively saved by a sonographer. Specifically, a review of an outlying measurement value for a particular anatomical feature of a fetus during an examination review may not be possible due to the absence of a corresponding ultrasound image. An outlying measurement value is a value that is extreme with respect to other measurement values of the same anatomical feature. Even if the ultrasound images were saved, the saved ultrasound images are not correlated with the measurement values. Without such correlation, a review of the saved measurement values can be difficult, since matching an ultrasound image to the corresponding measurement value can be tedious. For example, if a reviewer wants to examine an outlying measurement value, the invalidation or verification of the outlying measurement value can only be accomplished by an exhaustive review of all stored ultrasound images.

In light of these concerns, what is needed is a method and a system for storing and managing both the measurement values and their corresponding ultrasound images to facilitate an efficient ultrasound examination and an effective review of the saved measurement values and the ultrasound images.

SUMMARY OF THE INVENTION

A method and a system for storing and managing dimensional measurement values and the underlying ultrasound images utilize a report generator that operates to generate an examination report of an ultrasound examination having saved measurement values. The operations of the report generator allow an expedient access to the corresponding ultrasound images that were used to derive the measurement values. In addition, the report generator operates to automatically save the ultrasound image when a measurement value that was computed from that ultrasound image is saved. This feature ensures that for each saved measurement value,.the corresponding ultrasound image is also saved. The system utilizes ultrasound waves to image various anatomical features of a patient or a fetus. Examples of anatomical features that may be imaged by the system include the femur, the humerus, and the fetus head. These ultrasound images are used to compute measurements of the anatomical features.

The system includes an ultrasonic scanhead, a processing unit, an input device, and a display device. The scanhead includes an array of piezoelectric elements to transmit sound waves and to receive echoes of the transmitted ultrasound waves that are reflected from an anatomical feature of interest. The scanhead operates to convert the received echoes into electrical signals. The scanhead is electrically coupled to the processing unit, which generates an ultrasound image of the anatomical feature from the electrical signals. The input device functions as a user interface and may include a standard computer keyboard and a computer mouse. The display device may be a CRT or an LCD monitor.

The processing unit of the system includes a scanhead controller, memory, the report generator, a removable storage device, a network interface, and a processor. The scanhead controller is operatively connected to the ultrasonic scanhead to control the transmitting and receiving operations of the scanhead. The removable storage device may utilize one of a number of removable storage media that are currently available, such as a writeable CD, a DVD, or a magneto-optical storage medium.

The report generator of the processing unit is configured to operate with the processor to generate an examination report that can be displayed on the display device. The report generator performs many of the procedures that are necessary to generate the examination report. The report generator may be implemented in the processing unit as hardware and/or software. The report generator includes a measurement computer, an automatic ultrasound image saver, a measurement-to-image associator, and a data analyzer. The measurement computer operates to compute a dimensional measurement of an anatomical feature depicted in an ultrasound image. The automatic ultrasound image saver operates to automatically save an underlying ultrasound image when a measurement value that was derived from the underlying ultrasound image is saved during an ultrasound examination. The measurement-to-image associator operates to link each measurement value to its corresponding ultrasound image. The data analyzer operates to derive an analysis based on the saved measurement values. The analysis may indicate any abnormalities of the patient or the fetus that was examined. In the case of a fetal examination, the data analyzer may determine an estimated gestational age of the fetus.

The method in accordance with the present invention includes a step in which an ultrasound image of an anatomical feature is captured using a well known ultrasound imaging technique. Next, a dimensional aspect of the anatomical feature depicted in the ultrasound image is measured using the measurement computer to derive a measurement value. The measurement value is then saved by a sonographer. In response to this saving operation, the automatic ultrasound image saver of the report generator automatically saves the ultrasound image to ensure that for each saved measurement value, a corresponding ultrasound image is also saved. Additional measurement values for the same anatomical feature and/or other anatomical features of the patient or the fetus may then be derived and saved from additionally captured ultrasound images.

After all the measurement values of interest and the corresponding ultrasound images have been saved, an examination report is generated by the report generator of the system. The examination report can be electronically displayed on the display device of the system. The examination report includes the saved measurement values and their corresponding ultrasound images. In one embodiment, the examination report contains a number of virtual buttons. Each virtual button is designated with a specific measurement value. When a virtual button of a particular measurement value is activated, the examination report that is displayed on the display device is replaced with the ultrasound image that corresponds to the particular measurement value. In an alternative configuration, the corresponding ultrasound image is displayed in a superimposed manner over the examination report when the virtual button is activated, such that the corresponding ultrasound image and most of the examination report are simultaneously visible on the display device. This feature provides an efficient means to invalidate or verify any outlying measurement values. In addition, this feature allows the viewer to selectively examine only the ultrasound images that are of interest without reviewing all the saved ultrasound images.

In another embodiment, the examination report includes a number of hyperlinks that are associated with the measurement values, instead of virtual buttons. The hyperlinks operate in the same manner as the virtual buttons. When a hyperlink that is associated with a particular measurement value is activated, e.g., by "clicking on" or "hovering" a cursor over the hyperlink, the examination report that is displayed on the display device is replaced with the ultrasound image that corresponds to the particular measurement value. In an alternative configuration, the corresponding ultrasound image is displayed in a superimposed manner over the examination report when the hyperlink is activated.

BRIEF DESCRIPTION OF THE DRAWINGS

FIG. 5 is a portion of an examination report having hyperlinks in accordance with another embodiment of the invention that is displayed on the display device.

DETAILED DESCRIPTION

Figure 1:
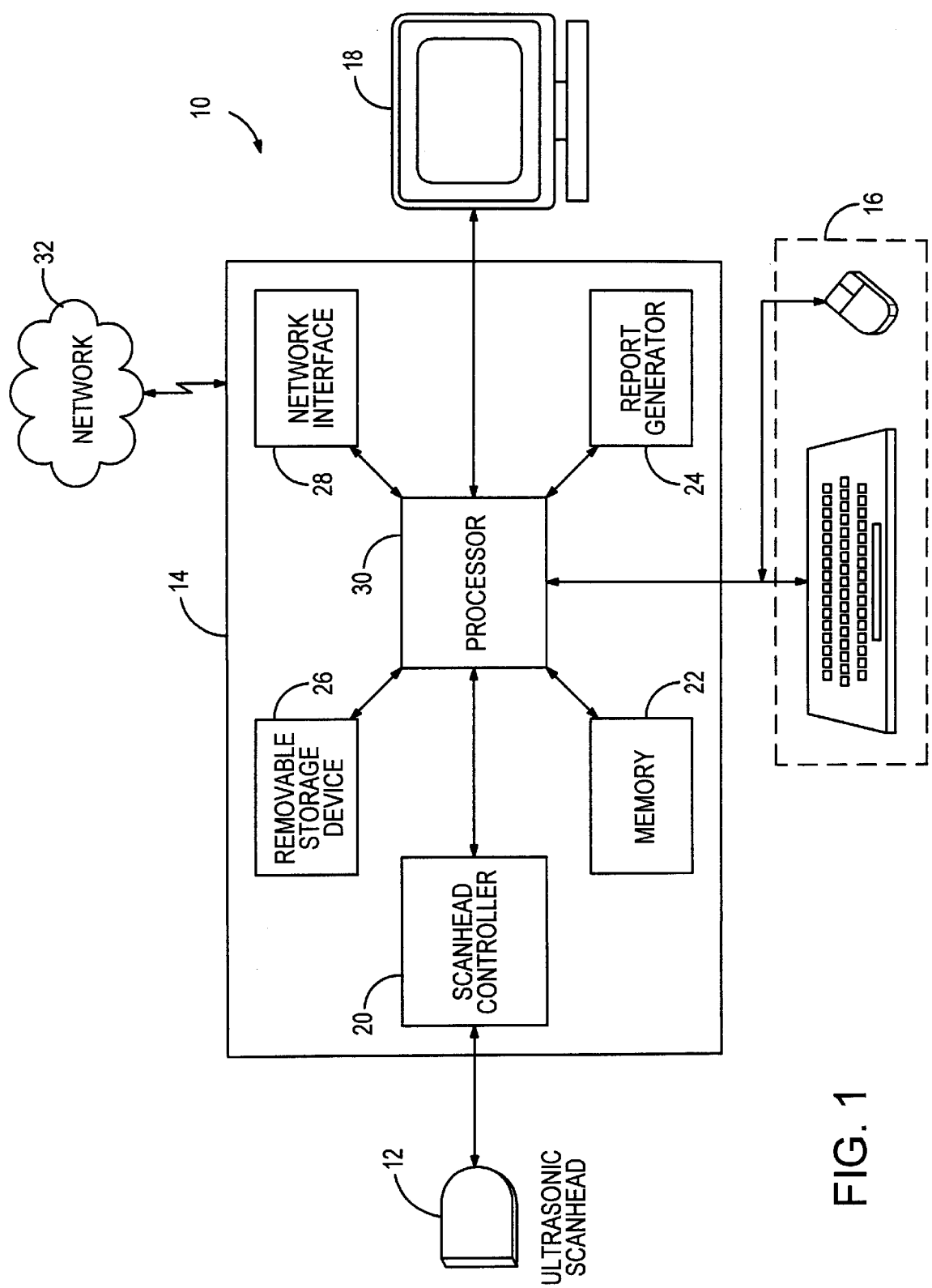
FIG. 1 is a schematic diagram of an ultrasound imaging system in accordance with the present invention.

With reference to FIG. 1, an ultrasound imaging system 10 in accordance with the present invention is shown. The system operates to image various anatomical features of a patient or a fetus during an ultrasound examination by transmitting ultrasound waves and then receiving echoes of the transmitted ultrasound waves that are reflected from an anatomical feature being examined. Examples of anatomical features that may be imaged by the system include the femur, the humerus and the head. These ultrasound images are used to compute dimensional measurements, such as femur length, humerus length and head circumference. The computed measurements and their corresponding ultrasound images can then be saved in the system to generate a report of the ultrasound examination. The manner in which the computed measurements and the corresponding ultrasound images are saved in the system ensures that for each saved measurement, its corresponding ultrasound image is also saved. In addition, the computed measurements and the corresponding ultrasound images are incorporated into the examination report, so that a user can easily navigate between the measurements to their corresponding ultrasound images within the examination report.

The ultrasound imaging system 10 includes an ultrasonic scanhead 12, a processing unit 14, an input device 16, and a display device 18. The ultrasonic scanhead includes an array of piezoelectric elements that generates ultrasound waves in response to electrical signals of proper voltage and frequency. As is well known in the art, the piezoelectric element array of the scanhead also generates electrical signals in response to mechanical vibrations caused by return echoes of the ultrasound waves. These return echoes are processed by the processing unit 14 to image an anatomical feature of interest.

The input device 16 may include a standard computer keyboard and a computer mouse, as shown in FIG. 1. The input device 16 is used as a user interface to control the functions of the system 10, such as initiating ultrasound imaging, computing a measurement for a particular anatomical feature, storing the computed measurement and the corresponding ultrasound image, displaying an examination report on the display device 18, and navigating through information incorporated in the displayed examination report. The display device 18 may be a conventional computer monitor, such as a CRT or an LCD monitor.

The processing unit 14 is designed to perform various signal processing procedures that are required for proper operation of the system 10. Included in the processing unit are a scanhead controller 20, memory 22, a report generator 24, a removable storage device 26, a network interface 28, and a processor 30. The scanhead controller 20 is operatively connected to the ultrasonic scanhead 12 to control the transmitting and receiving operations of the scanhead. The memory 22 of the processing unit may be a standard hard disk drive that is commonly found in a typical personal computer. The removable storage device 26 may utilize one of a number of removable storage media that are currently available, such as a writeable CD, a DVD, or a magneto-optical storage medium. The network interface 28 may include a modem or an ethernet card that allows the system 10 to be connected to a network 32. The network may be any type of network, such as a LAN, a WAN or the Internet.

Figure 2:
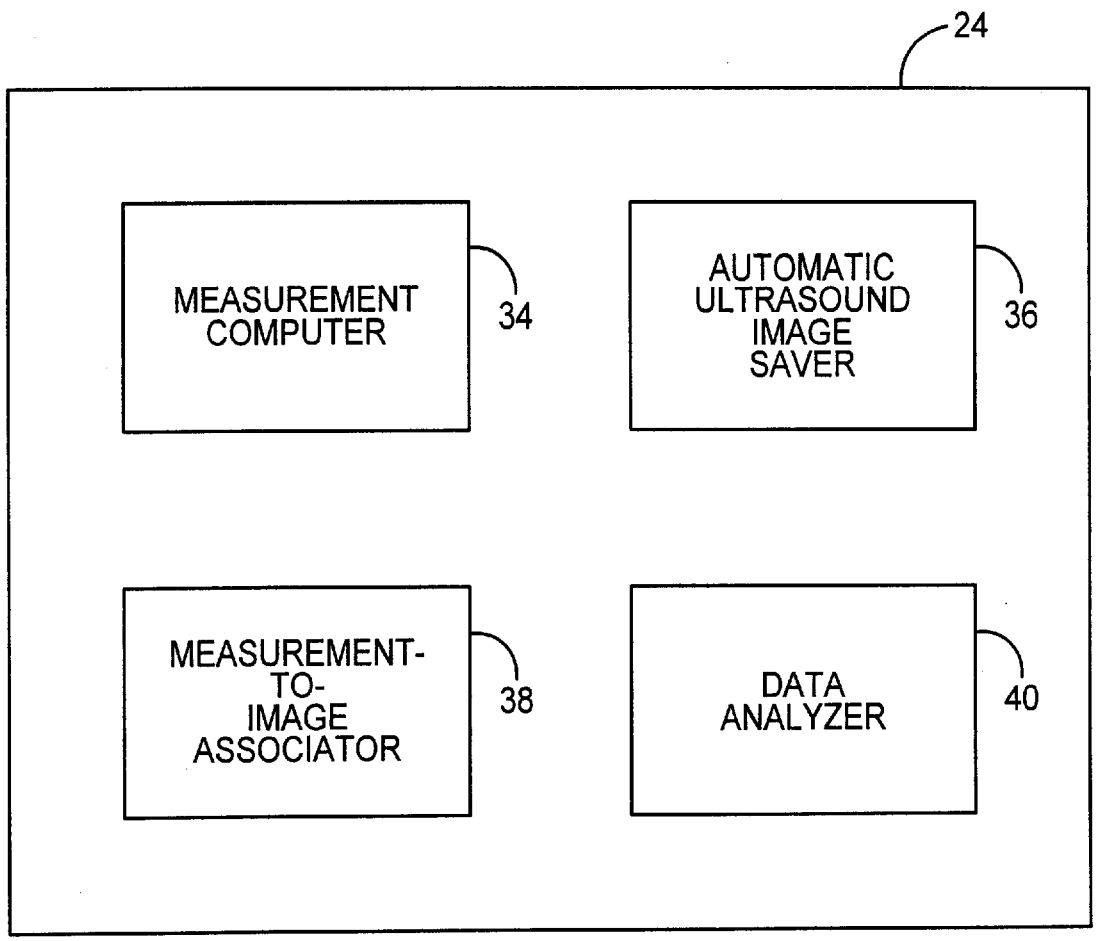
FIG. 2 is a block diagram showing the components of a report generator included in the system of FIG. 1.

The report generator 24 of the processing unit 14 is configured to operate with the processor 30 to generate an examination report that can be displayed on the display device 18. The report generator performs many of the procedures that are necessary to generate the examination report. The report generator may be implemented in the processing unit as hardware and/or software. The report generator includes a measurement computer 34, an automatic ultrasound image saver 36, a measurement-to-image associator 38, and a data analyzer 40, which are illustrated in FIG. 2. The measurement computer 34 is configured to assist a sonographer in measuring an anatomical feature in the displayed ultrasound image in a known manner. For example, the sonographer may indicate two reference points at the opposite ends of an anatomical feature, such as a femur of a fetus, that is depicted in an ultrasound image. The reference points may be indicated by using the mouse of the input device 16. After the two reference points have been indicated, the sonographer activates a control on the input device to initiate the measuring procedure. The activation signals the measurement computer to draw a line connecting the two reference points and to compute the length of the drawn line using predefined calibration parameters.

The automatic ultrasound image saver 36 of the report generator 24 operates to automatically save an ultrasound image when a corresponding measurement value is being saved under the direction of the sonographer. Thus, for each saved measurement value, its corresponding ultrasound image will also be saved. This feature ensures that a reviewer of the ultrasound examination can independently examine the underlying ultrasound image for a questionable measurement value. In addition to the automatic image saving feature, the measurement-to-image associator 38 of the report generator allows the report generator to link the saved measurement value with its corresponding ultrasound image, so that there is an association between the measurement value and the image. The association of the measurement value and the corresponding ultrasound image allows the report generator to create an examination report in which the measurement value and the corresponding ultrasound image are operatively coupled, such that the ultrasound image corresponding to a particular measurement value on the examination report can be found with a click of a button or a stroke of a key on the input device 16, without the need to review a large number of saved ultrasound images to find the desired ultrasound image.

The data analyzer 40 of the report generator 24 is configured to process the measurement values that were saved and to derive an analysis based on the measurement information. If a fetus was examined, the data analyzer may determine an estimated gestational age of the fetus from the measurement values. In addition, the data analyzer may indicate any abnormalities of the patient or the fetus by comparing the measurement values with established values for the particular size of the patient or, in the case of a fetus, the particular gestational age of the fetus. The analysis derived by the data analyzer is included in the examination report that will be generated by the report generator. The examination report, as displayed on the display device, will be described below.

Figure 3:
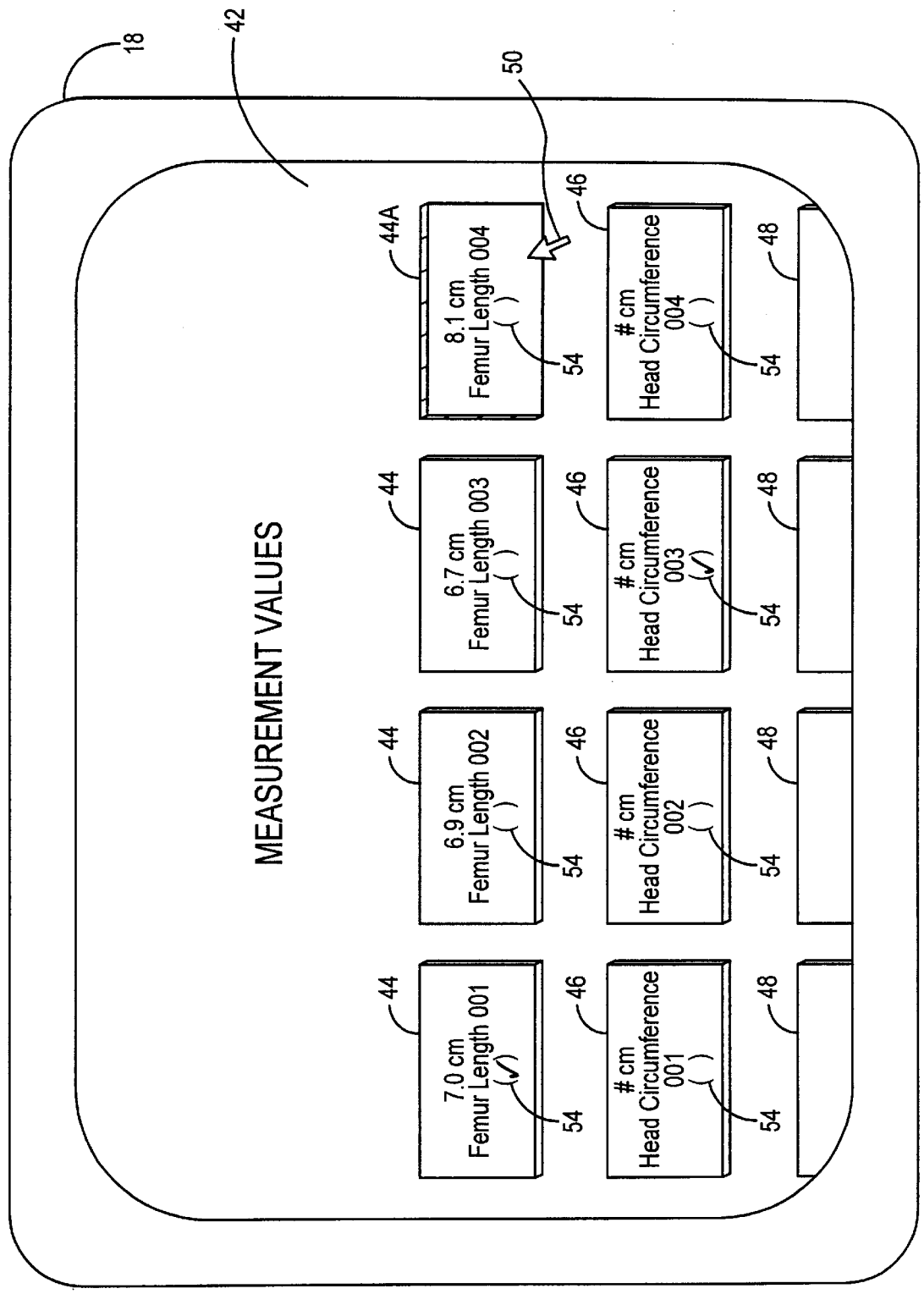
FIG. 3 is a portion of an examination report having virtual buttons in accordance with one embodiment of the invention that is displayed on a display device of the system of FIG. 1.
Figure 4:
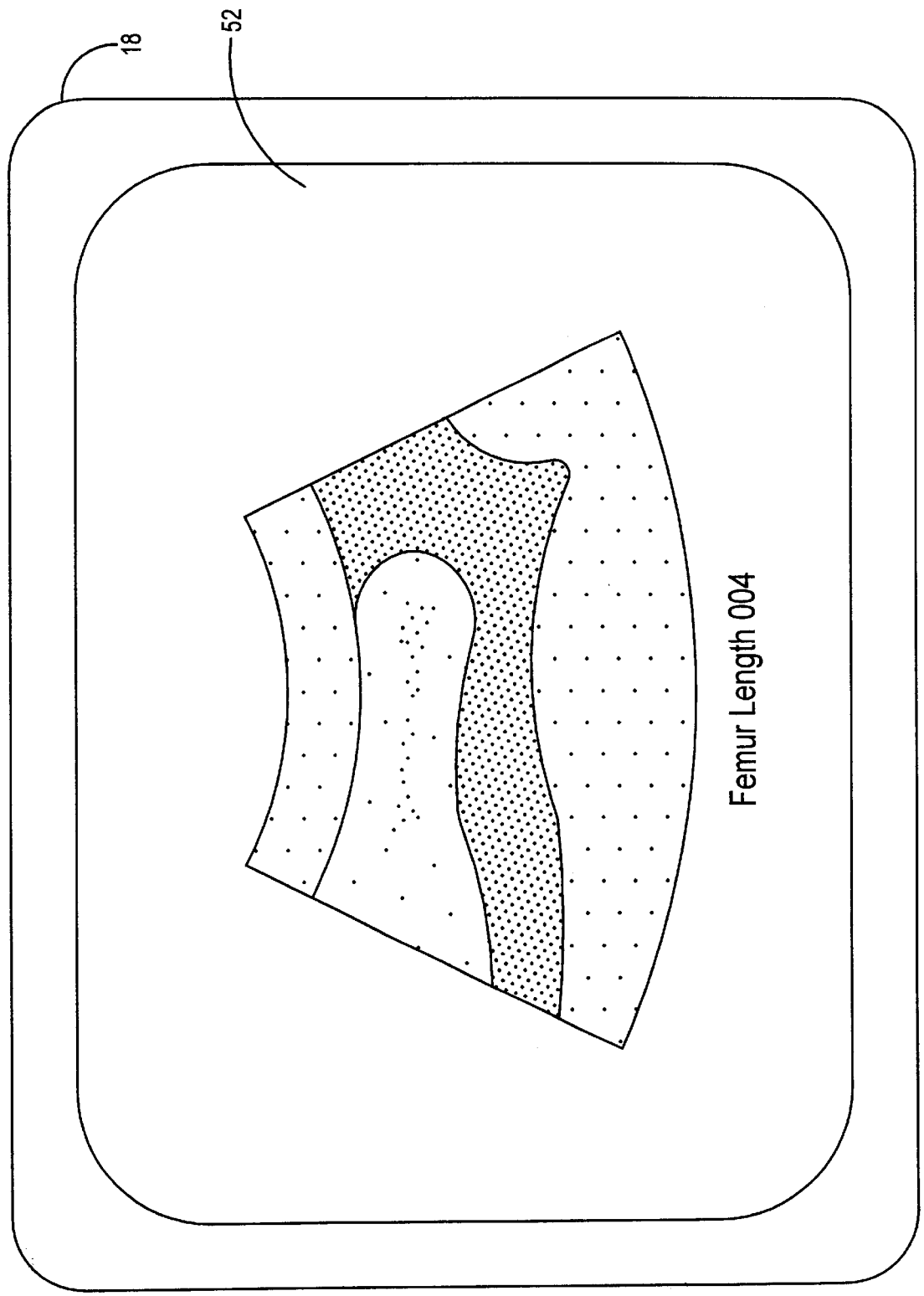
FIG. 4 is an exemplary ultrasound image that is displayed on the display device when one of the virtual buttons of FIG. 3 is activated.

FIG. 3 illustrates a portion of an examination report 42 for a fetus in accordance with one embodiment of the invention. The report is generated by the report generator 24 and is displayed on the display device 18. The examination report is shown to include a number of measurement values of the fetus that were computed during an ultrasound examination. Each measurement value is displayed on one of several virtual buttons 44, 44A, 46 and 48. The virtual buttons 44 are dedicated to measurement values of a femur length, while virtual buttons 46 are dedicated to measurement values of the head circumference. In the preferred embodiment, a text string that identifies a particular measurement value is also displayed on each of the buttons. The text strings are preferably typed into the system 10 prior to saving the measurement value during the ultrasound examination. In FIG. 3, a cursor 50 is positioned over the button 44A, which is being "pressed." The examination report 42 is configured to display an ultrasound image when the button having the corresponding measurement value is pressed. Therefore, the next screen that will be displayed on the display device will include an ultrasound image 52 which was used to compute the 8.1 cm femur length, which is shown in FIG. 4. In an alternative configuration, the ultrasound image is displayed along with the examination report when the corresponding virtual button is pressed, instead of replacing the displayed examination report. As an example, the pressing of the virtual button 44A may cause a reduced image of the ultrasound image 52 of FIG. 4 to be displayed over a particular region of the displayed examination report 42 of FIG. 3 (e.g., next to the virtual button 44A), such that the ultrasound image and most of the examination report are simultaneously visible on the display device. Preferably, the text string that was entered for the measurement value is also superimposed on the corresponding ultrasound image. This feature of measurement-to-image linkage allows a reviewer of the examination report to have almost an instant access to the ultrasound images that correspond to the measurement values in the examination report. Furthermore, since the report generator automatically saves the underlying ultrasound image when a measurement value is saved, the examination report will contain all the ultrasound images that were used to compute the measurement values.

The virtual buttons 44, 44A, 46 and 48 of the examination report 42 of FIG. 3 may also include checkbox fields 54 that can be checked or unchecked. As an example, the checkbox fields can be checked or unchecked by positioning the cursor 50 over the checkbox field of interest. The checkbox fields allow the operator of the ultrasound imaging system 10 to indicate the measurement values and/or their corresponding ultrasound images of the examination report that are to be sent to a destination, such as a remote computer system (not shown), through a network.

FIG. 5 shows a portion of an examination report 56 for a fetus in accordance with another embodiment of the invention. The report is generated by the report generator 24 and is displayed on the display device 18. The examination report includes the same measurement values that were shown in the examination report 42 of FIG. 3. The examination report 56 includes hyperlinks 58, 58A, 60 and 62 for the displayed measurement value. A hyperlink is an underlined text string that is commonly found on web sites on the Internet. Essentially, the buttons 44, 44A, 46 and 48 of the examination report 42 are replaced by the hyperlinks of the examination report 56. In FIG. 5, the cursor 50 is positioned over the hyperlink 58A, which is being "activated," as indicated by the underlined text "femur length 004" shown in boldface type. The activation of a hyperlink in the examination report 56 may involve positioning the cursor 50 over the desired hyperlink and "clicking on" an appropriate button on a mouse of the input device 16 of FIG. 1, or merely "hovering" the cursor over the desired hyperlink. Similar to the "pressing" of the button 44A in FIG. 3, the activation of the hyperlink 58A initiates the display of the ultrasound image 52 which was used to compute the 8.1 cm femur length. The ultrasound image 52 may be displayed on the display device 18 as a solitary image, replacing the examination report 56, or as a superimposed image over the examination report. The examination report 56 may also include a checkbox field 54 for each measurement value included in the examination report.

Figure 6:
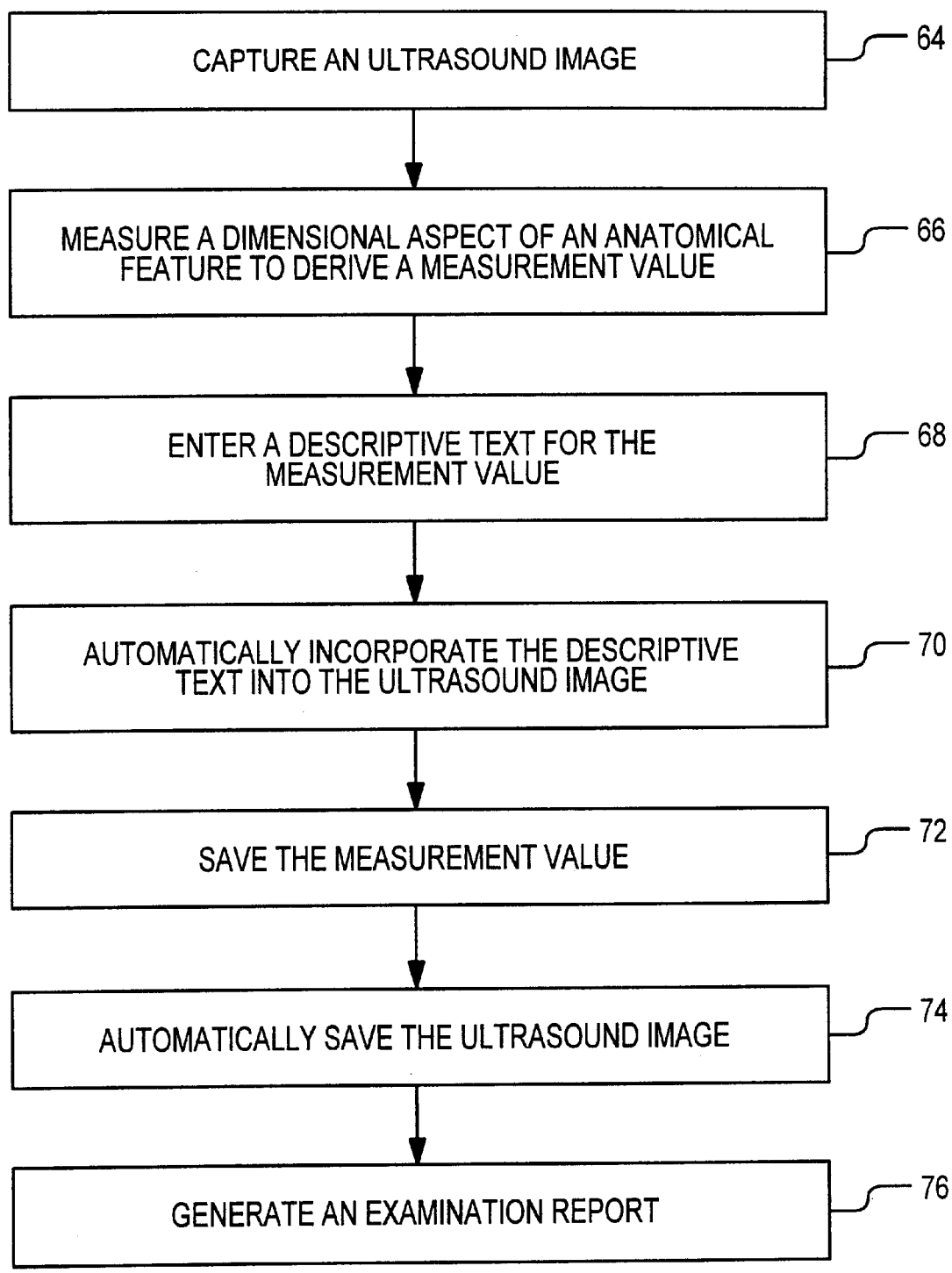
FIG. 6 is a flow diagram of a method of storing and managing measurement values, including corresponding ultrasound images, using the system of FIG. 1.

A method of storing and managing measurement values of anatomical features of a patient or a fetus, including the corresponding ultrasound images, using the ultrasound imaging system 10 of FIG. 1, will be described with reference to FIG. 6. At step 64, an ultrasound image of an anatomical feature is captured by scanning the ultrasonic scanhead 12 on a patient or a mother of the fetus on an area that coincides with the anatomical feature of interest, such as a femur or a humerus. In a well known manner, ultrasound waves are transmitted from the scanhead and then echoes of the ultrasound waves that have been reflected from the anatomical feature are received by the same scanhead. The echoes of the ultrasound waves are converted into electrical signals and transmitted to the processor 30 of the processing unit 14. The processor creates the ultrasound image of the anatomical feature by processing the received electrical signals. Next, at step 66, a dimensional aspect of the imaged anatomical feature is measured to derive a measurement value of the anatomical feature. For example, the length of the anatomical feature, e.g., a femur, may be measured during this step. The procedure for measuring an anatomical feature depicted in an ultrasound image is well known in the art.

At step 68, descriptive text is entered into the system for the measurement value by typing the text on the input device of the system. The descriptive text will appear with the measurement value in an examination report that will be subsequently generated. In response to step 68, the descriptive text is automatically incorporated into the ultrasound image that corresponds to the measurement value by the report generator, as indicated by step 70. This automatic step ensures that the ultrasound image will be stored in an annotated form for verification, if the ultrasound image is later saved. At step 72, the measurement value of the anatomical feature is saved by the sonographer, if the sonographer decides that it should saved. The sonographer may save the measurement value by pressing a button on the scanhead 12 or pressing a key on the input device 16. At step 74, the corresponding ultrasound image is automatically saved by the automatic ultrasound image saver 36 of the report generator 24. This automatic step ensures that for each measurement value saved, the corresponding ultrasound image is also saved. Steps 64 through 74 may be repeated on the same anatomical feature to derive redundant measurement information. Furthermore, steps 64 through 74 may be repeated on other anatomical features of the patient or the fetus to gather different dimensional measurements.

After all the measurement values of interest and the corresponding ultrasound images have been saved, an examination report is generated by the report generator 24 of the system 10, as indicated by step 76. The examination report can be electronically displayed on the display device 18. The examination report contains the saved measurement values. In addition, the examination report may include information that relates to the patient or the mother of the fetus. The examination report may also include an analysis derived from the saved measurement values by the data analyzer of the report generator. As an example, the analysis may indicate any abnormalities of the patient or the fetus. In the case of a fetal examination, the analysis may include an estimated gestational age of the fetus.

In one embodiment, the examination report contains a number of virtual buttons. Each virtual button includes the measurement value and the descriptive text that were entered prior to saving the measurement value. The virtual buttons allow a viewer of the examination report to examine the corresponding ultrasound image for each measurement value on the examination report. When a virtual button of a particular measurement value is activated, the examination report that is displayed on the display device 18 of the system 10 is replaced with the ultrasound image that corresponds to the particular measurement value. In an alternative configuration, the corresponding ultrasound image is displayed in a superimposed manner over the examination report when the virtual button is activated, such that the corresponding ultrasound image and most of the examination report are simultaneously visible on the display device. This feature provides an efficient means to invalidate or verify any outlying measurement values. In addition, this feature allows the viewer to selectively examine only the ultrasound images that are of interest without reviewing all the saved ultrasound images.

In another embodiment, the examination report contains a number of hyperlinks. Each hyperlink is associated with a saved measurement value. The hyperlink may be in a form of underlined descriptive text in which the descriptive text is the text that was entered prior to saving the measurement value. The hyperlinks operate in the same manner as the virtual buttons. When a hyperlink of a particular measurement value is activated, e.g., by "clicking on" or "hovering" a cursor over the hyperlink, the examination report that is displayed on the display device 18 is replaced with the ultrasound image that corresponds to the particular measurement value. In an alternative configuration, the corresponding ultrasound image is displayed in a superimposed manner over the examination report when the hyperlink is activated.

In either embodiment, each virtual button or hyperlink may also include a checkbox field that can be checked or unchecked by the viewer of the examination report. The ultrasound images that correspond to the measurement values having a checked field can then be collectively transmitted to a destination via the network 32. This feature allows the viewer to eliminate an extra step of reviewing all the saved ultrasound images prior to transmission. The review of the ultrasound images for transmission can be accomplished during the examination review when the measurement values and the corresponding ultrasound images are reviewed for any errors.

What is claimed is:

1. A method of managing dimensional measurements of target structures and ultrasound images of said target structures that were used to derive said dimensional measurements comprising steps of:

computing a dimensional measurement of a target structure from a given ultrasound image of said target structure;

saving said dimensional measurement of said target structure in a storage medium, including automatically saving said given ultrasound image of said target structure as separately stored but linked associated information of said dimensional measurement in response to said saving of said dimensional measurement of said target structure, wherein said dimensional measurement and said given ultrasound image are independently accessible.

2. The method of claim 1 further comprising a step of generating an examination report containing said dimensional measurement that can be displayed on a display device independently of said given ultrasound image from which said dimensional measurement was computed, said dimensional measurement on said examination report being operatively linked to said given ultrasound image such that said given ultrasound image can be displayed on said display device when a control that is associated with said dimensional measurement is activated, said step of generating said examination report including incorporating at least one dimensional measurement computed from at least one ultrasound image, wherein said at least one dimensional measurement is simultaneously displayed and each dimensional measurement is operatively linked to at least one ultrasound image from which said dimensional measurement is computed.

3. The method of claim 2 wherein said step of generating said examination report includes creating a virtual button for said dimensional measurement on said examination report, said virtual button being said control that displays said given ultrasound image of said target structure when said virtual button is activated.

4. The method of claim 2 wherein said step of generating said examination report includes creating a hyperlink for said dimensional measurement on said examination report, said hyperlink being said control that displays said given ultrasound image of said target structure when said hyperlink is activated.

5. The method of claim 2 further comprising steps of:
selecting particular ultrasound images from a first plurality of saved ultrasound images by indicating selections on fields that are associated with a second plurality of corresponding dimensional measurements, said first plurality including said given ultrasound image and said second plurality including said dimensional measurement that corresponds to said given ultrasound image; and
transmitting only said particular ultrasound images from said plurality of said saved ultrasound images to a network.

6. The method of claim 1 further comprising a step of entering descriptive text for said dimensional measurement, said descriptive text being associated with said dimensional measurement and said given ultrasound image of said target structure.

7. The method of claim 6 further comprising a step of incorporating said descriptive text onto said given ultrasound image of said target structure, said incorporating step being executed prior to completion of said automatic saving of said given ultrasound image of said target structure.

8. The method of claim 1 further comprising a step of forming said given ultrasound image by processing an echo of transmitted ultrasound that has been reflected from said target structure.

9. The method of claim 1 wherein said step of computing said dimensional measurement of said target structure is a step of computing said dimensional measurement of an anatomical structure of a person.

10. A diagnostic system comprising;
measuring means configured to receive an ultrasound image of a target structure for computing a dimensional measurement value of said target structure from said ultrasound image;
storage means operatively coupled to said measuring means for storing said dimensional measurement value and said ultrasound image such that said dimensional measurement value and said ultrasound image are independently accessible;
display means operatively coupled to said storage means for displaying an examination report that includes said dimensional measurement value and said ultrasound image, said examination report having a particular report format in which said dimensional measurement value and said ultrasound image are operatively linked while being independently accessible; and
report generating means operatively coupled to said display means and said storage means for generating said examination report in said particular report format from at least said dimensional measurement and said ultrasound image, said report generating means being configured to automatically save said ultrasound image in said storage means in response to a single control signal to save said dimensional measurement value in said storage means, said report generating means being configured to define said particular report format for displaying said examination report on said display means.

11. The system of claim 10 wherein said report generating means is configured to generate said examination report in which said dimensional measurement value is operatively linked with said ultrasound image such that said ultrasound image is displayed on said display means when a control on said examination report that is associated with said dimensional measurement value is activated.

12. The system of claim 11 wherein said report generating means is configured to generate said examination report in which said control on said examination report is in a form of a virtual button that can be activated to display said ultrasound image on said display means.

13. The system of claim 11 wherein said report generating means is configured to generate said examination report in which said control on said examination report is in a form of a hyperlink that can be activated to display said ultrasound image on said display means.

14. The system of claim 10 further comprising a network interface operatively coupled to said report generator, said network interface being configured to transmit designated ultrasound images to a network.

15. The system of claim 14 wherein said report generating means is configured to generate said examination report that includes a selectable field for each saved dimensional measurement value of a particular target structure, said selectable field being a parameter for selection of said designated ultrasound images for transmission to said network.

16. The system of claim 10 wherein said report generating means includes a means for automatically saving said ultrasound image in response to a command to save said dimensional measurement value.

17. The system of claim 10 further comprising:
transceiving means for transmitting ultrasound waves and receiving an echo of said transmitted ultrasound waves reflected from said target structure of a subject, said target structure being an anatomical feature of said subject; and
imaging means operatively coupled to said transceiving means for forming said ultrasound image from said echo of said transmitted ultrasound waves.

18. A method of generating an ultrasound examination report comprising steps of:
forming an ultrasound image of an anatomical feature of a subject;
measuring a dimensional aspect of said anatomical feature of said subject by examining said ultrasound image to derive a measurement value, said ultrasound image thereby being a corresponding ultrasound image with respect to said measurement value;
automatically saving said corresponding ultrasound image in response to a saving operation of said measurement value of said anatomical feature, said saving operation of said measurement value being initiated manually, said automatic saving including storing said corresponding ultrasound image separately from said measurement value while forming a permanent link between said measurement value and said corresponding ultrasound image; and generating said ultrasound examination report utilizing at least one said measurement value, said ultrasound examination report being in a format in which each measurement value is electronically displayed.

19. The method of claim 18 wherein said step of generating said ultrasound examination report is a step of generating said ultrasound examination report in which said measurement value is displayed on said ultrasound examination report and in which said storage of said corresponding ultrasound image is operatively linked to said ultrasound examination report but not displayed on said ultrasound examination report, said corresponding ultrasound image being operatively linked such that said corresponding ultrasound image is displayed when a specific control on said ultrasound examination report is activated, said specific control being associated with said measurement value.

20. The method of claim 18 wherein said step of generating said ultrasound examination report includes creating a virtual button on said ultrasound examination report, said virtual button being associated with said measurement value such that said corresponding ultrasound image is displayed when said virtual button is activated.

21. The method of claim 18 wherein said step of generating said ultrasound examination report includes creating a hyperlink on said ultrasound examination report, said hyperlink being associated with said measurement value such that said corresponding ultrasound image is displayed when said hyperlink is activated.

22. The method of claim 18 further comprising a step of entering descriptive text for said measurement value of said anatomical feature, including recording said descriptive text on said corresponding ultrasound image.

* * * * *